(12) United States Patent
Walters

(10) Patent No.: US 10,481,089 B2
(45) Date of Patent: Nov. 19, 2019

(54) OPTICAL DETECTION SYSTEM WITH TILTED SENSOR

(71) Applicant: Integrated Plasmonics Corporation, San Francisco, CA (US)

(72) Inventor: Robert Joseph Walters, San Francisco, CA (US)

(73) Assignee: INTEGRATED PLASMONICS CORPORATION, San Francisco, CA (US)

( * ) Notice: Subject to any disclaimer, the term of this patent is extended or adjusted under 35 U.S.C. 154(b) by 0 days.

(21) Appl. No.: 14/775,266

(22) PCT Filed: Dec. 3, 2013

(86) PCT No.: PCT/US2013/072932
§ 371 (c)(1),
(2) Date: Sep. 11, 2015

(87) PCT Pub. No.: WO2014/158248
PCT Pub. Date: Oct. 2, 2014

(65) Prior Publication Data
US 2016/0018329 A1    Jan. 21, 2016

Related U.S. Application Data

(60) Provisional application No. 61/778,311, filed on Mar. 12, 2013, provisional application No. 61/794,022, filed on Mar. 15, 2013.

(51) Int. Cl.
*G01N 21/552*    (2014.01)

(52) U.S. Cl.
CPC .................................. *G01N 21/553* (2013.01)

(58) Field of Classification Search
CPC .. G01N 21/554; G01N 21/553; G01N 21/658; G01N 2021/258
(Continued)

(56) References Cited

U.S. PATENT DOCUMENTS

| 4,516,857 A | 5/1985 | Preston et al. |
| 4,659,222 A | 4/1987 | Ekholm |

(Continued)

FOREIGN PATENT DOCUMENTS

| EP | 1 217 426 A1 | 6/2002 |
| WO | 1998/034098 A1 | 8/1998 |

(Continued)

OTHER PUBLICATIONS

Olga Telezhnikova and Jiří Homola, "New approach to spectroscopy of surface plasmons," Opt. Lett. 31, 3339-3341 (2006).*

(Continued)

*Primary Examiner* — Tri T Ton
*Assistant Examiner* — Rufus L Phillips
(74) *Attorney, Agent, or Firm* — Chen Yoshimura LLP

(57) ABSTRACT

A detection system includes a planar plasmonic element for analyzing an analyte, the plasmonic element having dielectric and metallic regions, the plasmonic element emitting light that carries detected information; and a planar two-dimensional image sensor positioned in non-parallel angled relationship with respect to a plane of the plasmonic element to enhance a spatial image resolution for the light that carries detected information with respect to at least a portion of the light.

3 Claims, 4 Drawing Sheets

(58) Field of Classification Search
USPC ......... 356/445, 446, 630; 359/809, 387, 245
See application file for complete search history.

(56) References Cited

U.S. PATENT DOCUMENTS

| | | | |
|---|---|---|---|
| 4,767,719 A * | 8/1988 | Finlan ................ | G01N 21/553 324/71.5 |
| 5,116,759 A | 5/1992 | Klainer et al. | |
| 5,644,512 A | 7/1997 | Chernoff et al. | |
| 5,674,457 A | 10/1997 | Williamsson et al. | |
| 5,846,843 A * | 12/1998 | Simon ................ | G01N 21/554 385/12 |
| 5,925,878 A * | 7/1999 | Challener ............ | G01N 21/211 250/225 |
| 5,955,378 A * | 9/1999 | Challener ............ | G01N 21/553 356/318 |
| D433,150 S | 10/2000 | Wahlqvist et al. | |
| 6,838,650 B1 | 1/2005 | Toh | |
| 7,466,409 B2 | 12/2008 | Scherer et al. | |
| 7,768,654 B2 * | 8/2010 | Cui ...................... | G01N 21/553 356/521 |
| 8,054,462 B2 * | 11/2011 | Chyba ................. | G01J 1/04 356/301 |
| 8,076,128 B2 | 12/2011 | Liederman et al. | |
| 8,231,268 B2 | 7/2012 | Krol et al. | |
| 8,284,401 B2 | 10/2012 | Choi et al. | |
| 8,368,897 B2 * | 2/2013 | Reilly ................. | G01J 3/02 356/445 |
| 2001/0026943 A1 * | 10/2001 | Dickopf .............. | G01N 21/553 436/164 |
| 2001/0031503 A1 * | 10/2001 | Challener ............ | G01N 21/553 436/518 |
| 2002/0001085 A1 * | 1/2002 | Dickopf .............. | G01N 21/253 356/445 |
| 2005/0053974 A1 * | 3/2005 | Lakowicz .......... | G01N 21/4788 435/6.12 |
| 2005/0114332 A1 | 5/2005 | Lee et al. | |
| 2006/0034729 A1 | 2/2006 | Poponin | |
| 2007/0070347 A1 | 3/2007 | Scherer et al. | |
| 2008/0135739 A1 | 6/2008 | Kim et al. | |
| 2009/0213382 A1 * | 8/2009 | Tracy ................. | G01N 21/253 356/445 |
| 2010/0039648 A1 | 2/2010 | Garcia da Fonseca | |
| 2010/0046060 A1 | 2/2010 | Lee et al. | |
| 2010/0128269 A1 * | 5/2010 | Chinowsky .......... | G01N 21/553 356/369 |
| 2010/0157306 A1 | 6/2010 | Choi et al. | |
| 2011/0085167 A1 | 4/2011 | Guan et al. | |
| 2011/0111487 A1 | 5/2011 | Goh et al. | |
| 2012/0225475 A1 | 9/2012 | Wagner et al. | |
| 2014/0176939 A1 | 6/2014 | Shah | |

FOREIGN PATENT DOCUMENTS

| | | |
|---|---|---|
| WO | 2006/009724 A2 | 1/2006 |
| WO | 2011/106057 A2 | 9/2011 |
| WO | 2012/054351 A2 | 4/2012 |
| WO | 2014/089120 A1 | 6/2014 |
| WO | 2014/123613 A1 | 8/2014 |
| WO | 2014/143234 A1 | 9/2014 |
| WO | 2014/143235 A1 | 9/2014 |

OTHER PUBLICATIONS

U.S. Appl. No. 14/095,971, filed Dec. 3, 2013.
U.S. Appl. No. 14/648,843, filed Jun. 1, 2015.
U.S. Appl. No. 14/766,551, filed Aug. 7, 2015.
U.S. Appl. No. 14/774,990, filed Sep. 11, 2015.
U.S. Appl. No. 14/775,299, filed Sep. 11, 2015.
International Search Report (ISR) issued in PCT/US2013/072927 dated Apr. 2014.
Written Opinion (PCT/ISA/237) issued in PCT/US2013/072927 dated Apr. 2014.
Huang et al., "Micro-hole drilling with femtosecond fiber laser", SPIE Paper No. 8607-19, Photonics West 2013, Feb. 2-7, 2013.
International Search Report (ISR) issued in PCT/US2013/072929 dated Apr. 2014.
Written Opinion (PCT/ISA/237) issued in PCT/US20131072929 dated Apr. 2014.
International Search Report (ISR) issued in PCT/US2013/072930 dated Apr. 2014.
Written Opinion (PCT/ISA/237) issued in PCT/US2013/072930 dated Apr. 2014.
International Search Report (ISR) issued in PCT/US2013/072932 dated Apr. 2014.
Written Opinion (PCT/ISA/237) issued in PCT/US2013/072932 dated Apr. 2014.
International Search Report (ISR) issued in PCT/US2013/072936 dated Apr. 2014.
Written Opinion (PCT/ISA/237) issued in PCT/US2013/072936 dated Apr. 2014.
Fiedler, "Incoherent Broad-Band Cavity-Enhanced Absorption Spectroscopy", 2005, Berlin.
Barron, "Basics OF UV-Visible Spectroscopy", Physical Methods in Chemistry and Nano Science, Jun. 5, 2010.
Chen et al., "A CMOS Image Sensor Integrated with Plasmonic Colour Filters", Plasmonics, Dec. 2012, vol. 7, Issue 4, (abstract) Springer Link.
Mansuripur et al., "Plasmonic nano-structures for optical data storage", Optics Express, Aug. 3, 2009, vol. 17, No. 16, pp. 14001-14014.
Genet et al., "Light in tiny holes", nature, Jan. 4, 2007, vol. 445, pp. 39-46.
Koerkamp et al., "Strong Influence of Hole Shape on Extraordinary Transmission through Periodic Arrays of Subwavelength Holes", Physical Review Letters, May 7, 2004, vol. 92, No. 18, pp. 183901-1-183901-4.
Jones et al., "Surface Plasmon assisted extraordinary transmission in metallic nanohole arrays and its suitability as a bio-sensor", Journal of Physics: Conference Series 307, IOP Publishing, 2011, pp. 1-7.
Tok et al., "Unidirectional broadband radiation of honeycomb plasmonic antenna array with broken symmetry", Optics Express, Nov. 7, 2011, vol. 19, No. 23, pp. 22731-22742.
Pacifici et al., "Universal optical transmission features in periodic and quasiperiodic hole arrays", Optics Express, Jun. 9, 2008, vol. 16, No. 12, pp. 9222-9238.
Singh et al., "Surface Plasmon Resonance Enhanced Transmission of Light through Gold-Coated Diffraction Gratings", Analytical Chemistry, May 15, 2008, vol. 80, No. 10, pp. 3803-3810.

* cited by examiner

OPTICAL DETECTION SYSTEM WITH TILTED SENSOR

BACKGROUND

In recent years, industries and academia have been making significant efforts towards development of technologies and infrastructures suitable for distributed diagnostics and home healthcare. One well-known, successful exemplary device in this endeavor is a portable glucose automonitoring device that can monitor the glucose level of the user by sampling of blood taken from a fingertip. Many efforts have been devoted to developing similar portable devices that can measure other biochemical substances. In this regime, what is needed from instrumental points of view is not high-precision, versatile measurement instruments that can detect a wide range of target analytes/substances with great accuracy, but low-cost, portable devices that can detect certain defined groups of target analytes/substances reliably and conveniently for the purpose of monitoring and diagnosing the users' physiological and biomedical conditions.

Numerous optical detection systems are in use to analyze biological specimens or other analytes. However, certain optical mechanisms require complex structures, not suited for portable devices. Especially when a higher resolution or detectability is required, it may be difficult to achieve the goal without increasing the device size or manufacturing costs.

BRIEF SUMMARY OF THE INVENTION

The present invention is directed to an optical detection system with a two-dimensional image sensor.

An object of the present invention is to provide an improved detection system for at least partially enhancing a spatial image resolution of a two-dimensional image sensor in the system.

To achieve these and other advantages and in accordance with the purpose of the present invention, as embodied and broadly described, in one aspect, the present invention provides a detection system that includes: a planar plasmonic element for analyzing an analyte, the plasmonic element having dielectric and metallic regions, the plasmonic element emitting light that carries detected information; and a planar two-dimensional image sensor positioned in non-parallel angled relationship with respect to a plane of the plasmonic element to enhance a spatial image resolution for the light that carries detected information with respect to at least a portion of the light.

In another aspect, the present invention provides a detection system that includes an optical detection unit for analyzing an analyte, the optical detection unit emitting light that carries detected information to an exterior, the light having an optical axis along which the light propagates; and a planar two-dimensional image sensor disposed in a direction angularly offset from a plane perpendicular to the optical axis to enhance a spatial image resolution for the light that carries detected information with respect to at least a portion of the light.

In another aspect, the present invention provides the detection system according to any one of the two aspects described above, wherein the light has one or more predetermined directions in which the light exhibits greater changes in response to interaction with the analyte, and wherein the planar two-dimensional image sensor is tilted towards one of the one or more predetermined directions.

In another aspect, the present invention provides a device for detecting an analyte, comprising: a light source emitting substantially monochromatic light; a two-dimensional diffraction element that interacts with the light from the light source, the diffraction element having one or more features that can generate plasmon waves upon receipt of the light from the light source, at least some of the features being configured to interact with the analyte; and a two-dimensional image sensor facing the diffraction element at an angle to receive diffracted light from the diffraction element so as to detect a diffraction pattern projected thereto.

Additional features and advantages of the invention will be set forth in the description which follows and in part will be apparent from the description, or may be learned by practice of the embodiments of the invention disclosed herein. The other objectives and advantages of the invention will be realized and attained by the structure particularly pointed out in the written description and claims hereof and/or in the appended drawings.

It is to be understood that both the foregoing general description and the following detailed description are exemplary and explanatory, and are intended to provide further explanation of the invention as claimed in a patent(s) originating from this application.

DETAILED DESCRIPTION

As a device for optically detecting an analyte, the present inventor is concurrently filing a commonly owned PCT International Application No. PCT/US2013/072930, entitled "Plasmonic Projected Diffraction Sensor", which designates the U.S. and claims the benefit of U.S. provisional application Nos. 61/762,818 and 61/785,400, filed on Feb. 8, 2013 and Mar. 14, 2013, respectively, directed to a projected diffraction sensor having a plasmonic diffraction element. That PCT International Application PCT/US2013/072930 is hereby incorporated by reference in its entirety and is referred to as "the '003A PCT International Application" hereinafter. In this, and other optical detection schemes, light that has interacted with a specimen carries information on the specimen in various ways, and an image projected by such light is detected by a planar two-dimensional image sensor to analyze the pattern of the image and/or changes of the pattern.

Various types of two-dimensional image sensor are available: focal plane array (FPA) device, including a front or back illuminated charge-coupled device (CCD), a photon penetration depth dependent device, a photo-diode array (PDA), an avalanche photodiode (APD) array, a PMT array, or a front or back illuminated complementary metal-oxide semiconductor (CMOS) detector. They are constructed of a plurality of pixels two-dimensionally arranged in a certain pattern, typically a rectangular pattern.

Figure 1:
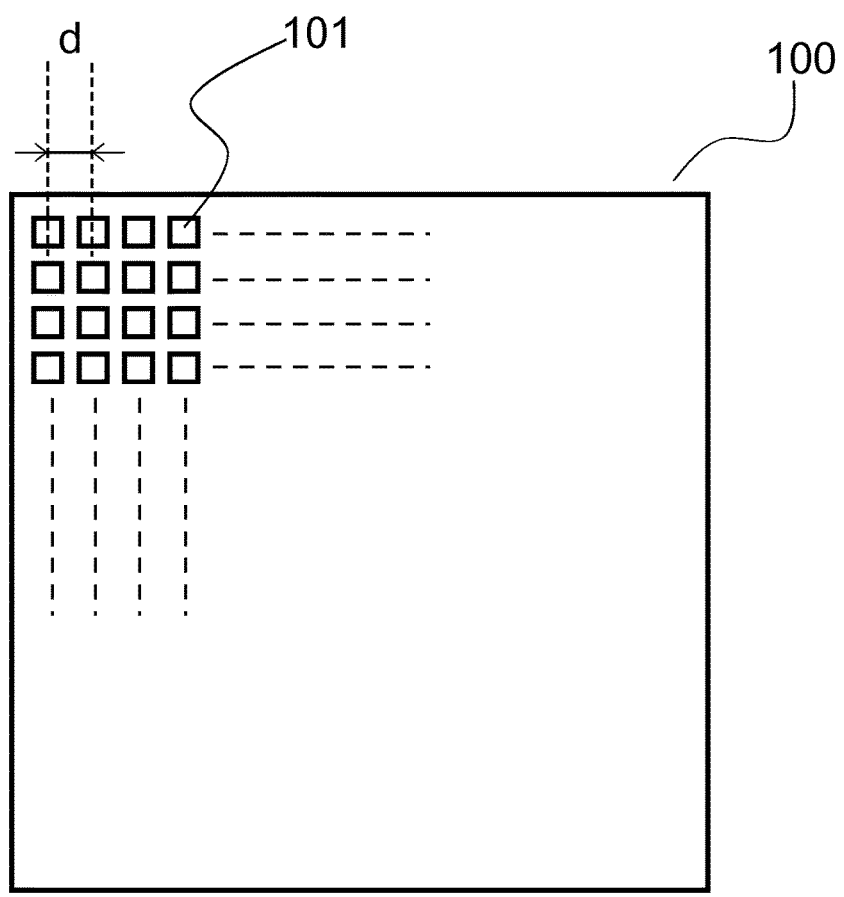
FIG. 1 is a schematic plan view of a two-dimensional image sensor.

FIG. 1 schematically shows a plan view of a planar two-dimensional sensor 100. A plurality of pixels 101, each of which can detect the intensity of the light it receives, are arranged in a rectangular pattern with a pitch d in this example. Recent development of the semiconductor technologies enables manufacture of a small-sized image sensor; the detection surface may be as small as a 1-inch square with the pixel pitch d approaching to 1 microns. Still, because the pixel arrangement has a finite length pitch, the spatial resolution is limited by the pitch d. Given an image to be analyzed, generally, the greater number of pixels it covers the image, the higher the resolution becomes. The light that carries the information on the specimen analyzed spans a finite area, (i.e., a finite solid angle). If a larger number of pixels are optically coupled with the light, more detailed information can be obtained by the image sensor. If the requisite number of pixels for analyzing the light occupy a larger area than the area projected by the light, various optical elements can be interposed between the light and the image sensor to expand the light so that the area illuminated by so processed light corresponds to the detection area of the image sensor. However, such optical elements require an additional space for the installment as well as adjustment and maintenance.

Figure 2:
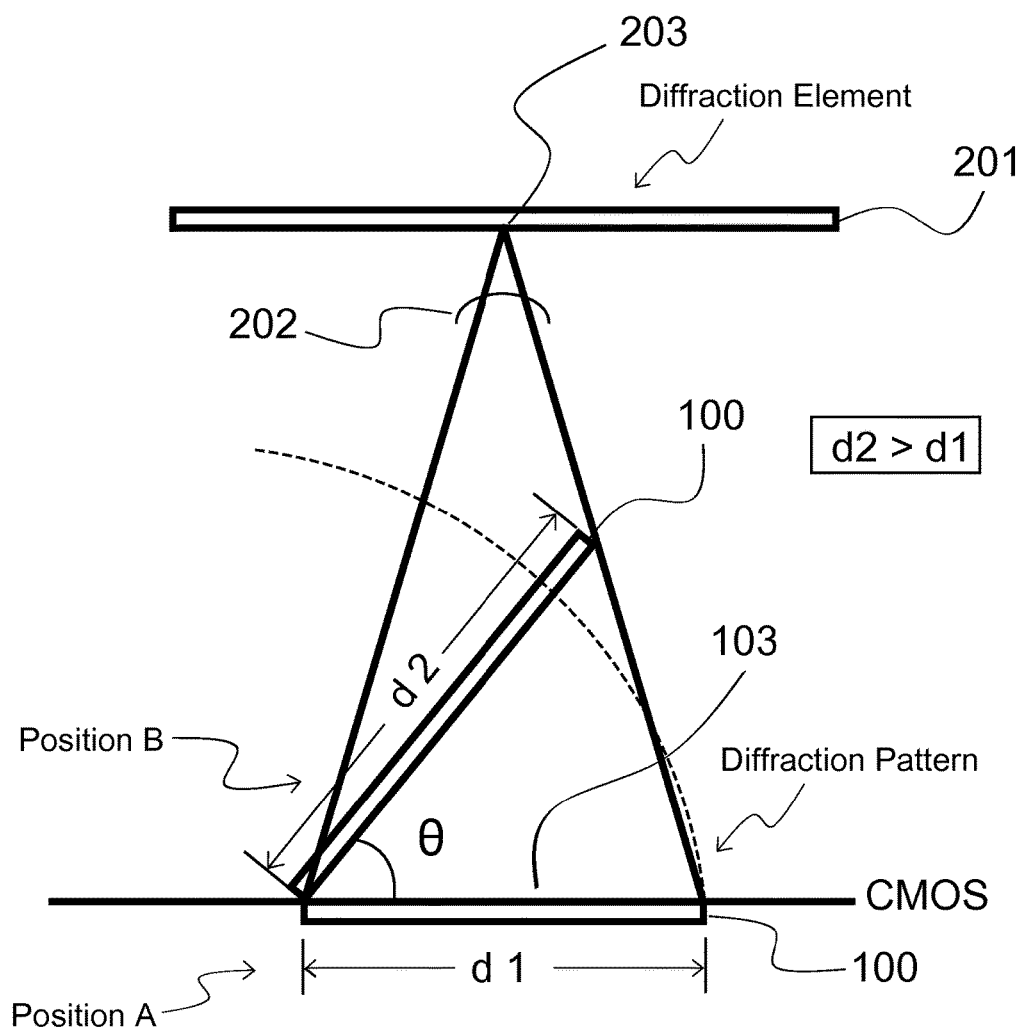
FIG. 2 is a side view of a detection system according to an embodiment of the present invention.

FIG. 2 schematically depicts a detection system according to an embodiment of the present invention. It shows a side view of the detection system. The detection surface 103 of the image sensor 100 has a plurality of pixels with prescribed intervals as shown in FIG. 1. Thus, the larger (longer on the side view) the detection surface, the greater the number of pixels associate with it. The reference numeral 201 indicates a portion (the bottom surface in this example) of an optical detection unit that emits light that carries information on a specimen analyzed. The detection unit 201 may be a planar plasmonic diffraction element disclosed in the '003A PCT International Application mentioned above. Although not shown in the figure, the detection unit 201 has other components, such as a container for containing the specimen, a light source for emitting probing light, and a collimator, etc., such as those shown in the '003A PCT International Application. In this example, the optical detection unit 201 emits light 202 that carries information on the specimen. As in the case of plasmonic diffraction element disclosed in the '003A PCT International Application, in this embodiment, the light 202 is diffraction light and forms a diffraction pattern having various distinguishable features if projected onto an image plane. The boundary lines in light 202 show a diffraction light cone of interest. Although the figure shows a point-like light emitting point 203 for simplicity of explanation, in actuality, the light is emitted from an area of finite size, such as plasmonic diffraction elements disclosed in the '003A PCT International Application.

Typically, this diffraction pattern is analyzed by the image sensor 100 positioned at Position A, which is parallel to the plane of the bottom surface of the optical detection unit (or planar plasmonic diffraction element) 201, or in other words, perpendicular to the optical axis in which the light 202 travels. As show in FIG. 2, the length d1 indicates an area that receives the light 202 of interest.

In this embodiment, the sensor 100 is tilted with respect to that plane and disposed at Position B. Then, the length d2 that receives the light 202 becomes longer than d1. Therefore, with a fixed number of pixels per length, more pixels cover the diffraction cone 202 in the tilted arrangement than in the parallel arrangement, thereby increasing the effective spatial resolution of the sensor with respect to the diffraction cone/light 202.

Figure 3:
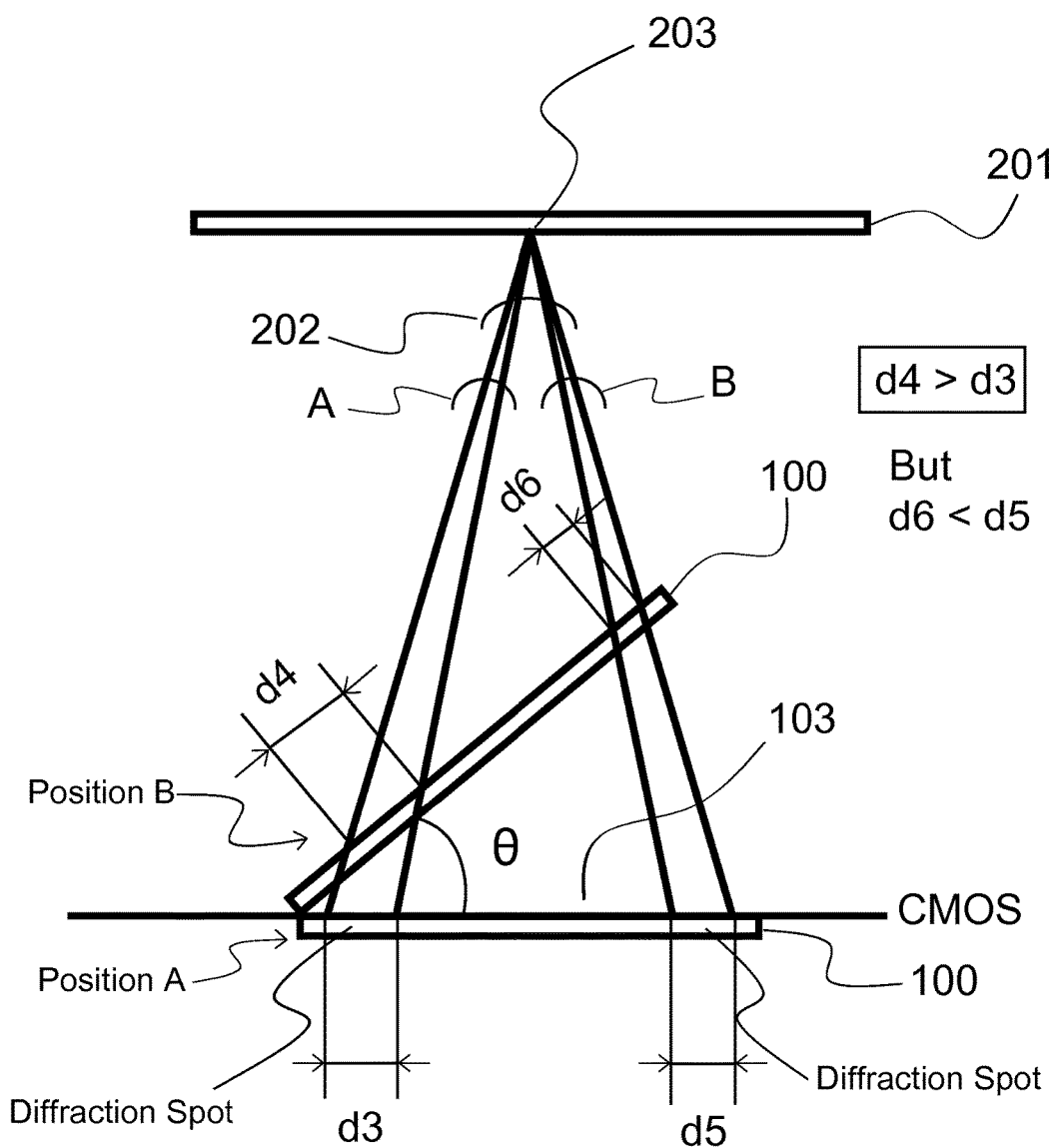
FIG. 3 is a side view of a detection system according to an embodiment of the present invention.

FIG. 3 shows another embodiment of the present invention. The figure shows a side view of a detection system comparable to FIG. 1. In this embodiment, the image sensor 100 is tilted so as to increase the areas of the image sensor spanned by some of fluxes of the diffraction cone 202. As shown in FIG. 3, with the tilted Position B, the flux A of the diffraction cone 202 spans a larger area than (larger length d4) than the area (shorter length d3) that would be spanned with the parallel arrangement. Thus, the effective spatial resolution of the image sensor is increased with respect to any features, such as diffraction spots, contained in the flux A. On the other hand, the flux B of the diffraction cone 202 may span a smaller area than (shorter length d6) than the area (longer length d5) that would be spanned with the parallel arrangement. Thus, the effective spatial resolution of the image sensor may be decreased with respect to the flux B. This arrangement is particularly useful when the diffraction pattern needs to be analyzed in more detail on one side of the diffraction pattern, for example.

With the tilted sensor arrangements as described above, areas on the detection surface of the image sensor that are further away from the detection system/diffraction element 201 have higher resolutions than areas closer to it. And in some instances, the resolution for the areas closer to the detection system 201 may have a resolution lower than the resolution with the parallel arrangement, as shown in FIG. 3. Yet, the improvement in spatial resolution with respect to at least a portion of the diffraction cone 202 as described above is advantageous in analyzing a fine pattern or small positional changes at the periphery of the diffraction pattern.

Moreover, the size of the system can be reduced by the tilted arrangement. As shown in FIGS. 2 and 3, the lateral dimension required for the image sensor is shortened with the tilted arrangements. Also, if desired and applicable, the image sensor 100 can be installed closer to the detection system 201 without sacrificing the spatial resolution for diffraction features of interest.

Figure 4:
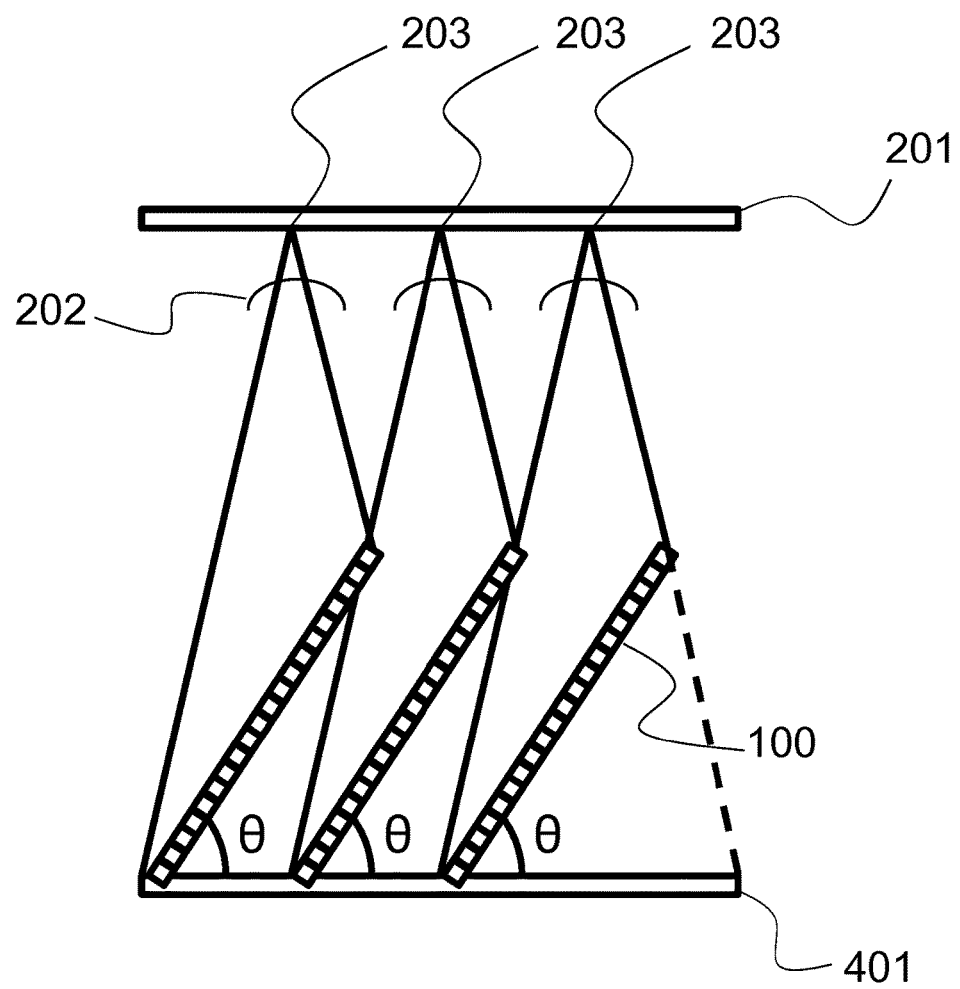
FIG. 4 is a side view of a detection system according to an embodiment of the present invention.

A size reduction is more dramatic when a plurality of two-dimensional image sensors or detection areas are employed to analyze a plurality of diffraction cones, for example. FIG. 4 shows such an arrangement according to another embodiment of the present invention. As shown in FIG. 4, a plurality of tilted image sensors 100 are disposed laterally to detect a plurality of corresponding diffraction cones 202. Since each diffraction cone need not project separate and distinct diffraction patterns on a horizontal plane 401, which would be required if the parallel arrangement is employed, the elements 203 that emit respective diffraction cones as well as the image sensors 100 may be laterally disposed closer to each other, and the overall lateral dimensions of the system/device can be reduced significantly. Moreover, in some applications, the diffraction pattern/features only on the peripheral portion of the diffraction pattern (lower left portion in FIG. 4; corresponding to an area indicated by d4 and its vicinity in FIG. 3) as well as possibly the intensity of the zero-th order diffraction at the center may be of interest. In such cases, only a certain left portion of the image sensor 100 can be provided in a single unit or multiple unit arrangements shown in FIGS. 2-4. For example, an image sensor having a detection area corresponding to only the left half or smaller portion of the image sensor 100 shown in FIG. 4 may be arranged laterally. Then, the elements 203 and the image sensors can be arranged further closer to each other, achieving a further reduction in lateral dimensions.

The light or light cone 202 may have particular diffraction features that need to be analyzed in one or more particular directions. For example, as disclosed in the '003A PCT International Application, when the diffraction element (corresponding to light emitting point 203 in the figures) has a particular directionality in its pattern and/or when the probing light is linearly polarized in a particular direction, the resulting diffraction pattern may have greater detectable changes in its pattern/diffraction spots in a certain direction(s) associated with these inherent directions the system has. In such a case, it is preferable to tile the image sensor 100 towards such a direction so that the effective resolution can be increased for such features of interest.

As shown in FIG. 1, two-dimensional image sensors typically have arrangement direction along which pixels are arranged, such as the column direction and the row direction. Also, an image sensor may have different pitches in horizontal and vertical directions. The direction in which the image sensor is tiled may be determined by taking into account these directional aspects of the image sensor.

To manufacture the system and embodiments of the present invention, the methods described in the '003A PCT International Application can be applied, for example. Commercially available CMOS sensors can be used, as is or as appropriately modified, for the image sensor 100. Also the driving and signal processing schemes and structure, and any details of the plasmonic element or optical detection unit described above are found in the '003A PCT International Application. Furthermore, the two-dimensional image sensor 401 may be combined with the detection unit 201 with an appropriate frame structure to create a unified device/system.

It will be apparent to those skilled in the art that various modifications and variations can be made without departing from the spirit or scope of the invention. Thus, it is intended that the disclosed embodiments cover modifications and variations that come within the scope of the claims that eventually issue in a patent(s) originating from this application and their equivalents. In particular, it is explicitly contemplated that any part or whole of any two or more of the embodiments and their modifications described above can be combined in whole or in part.

What is claimed is:

1. A detection system comprising:
    a planar plasmonic element for analyzing an analyte, the plasmonic element having dielectric and metallic regions, the plasmonic element emitting light that carries detected information, said light having an optical axis along which said light propagates, said optical axis being perpendicular to a plane of the planar plasmonic element; and
    a planar two-dimensional image sensor positioned in non-parallel angled relationship with respect to a plane perpendicular to said optical axis of said light that enters the planar two-dimensional image sensor so as to enhance a spatial image resolution for said light that carries detected information with respect to at least a portion of said light,
    wherein the planar two-dimensional image sensor is a CMOS sensor and is positioned directly below the planar plasmonic element without any other intervening optical elements between the planar plasmonic element and the CMOS sensor.

2. The detection system according to claim 1, wherein said light has one or more predetermined directions in which said light exhibits greater changes in response to interaction with the analyte, and
    wherein the planar two-dimensional image sensor is tilted towards one of said one or more predetermined directions.

3. A device for detecting an analyte, comprising:
    a light source emitting substantially monochromatic light;
    a two-dimensional diffraction element that interacts with the light from the light source, the diffraction element having one or more features that can generate plasmon waves upon receipt of the light from the light source, at least some of the features being configured to interact with the analyte so as to emit detection light that carries detected information, said detection light having an optical axis along which said detection light propagates, said optical axis being perpendicular to a plane of the two-dimensional diffraction element; and
    a two-dimensional image sensor facing the diffraction element at an angle to receive diffracted light from the diffraction element so as to detect a diffraction pattern projected thereto, the two-dimensional image sensor being disposed in a direction angularly offset from a plane perpendicular to said optical axis of said detection light that enters the two-dimensional image sensor,
    wherein the two-dimensional image sensor is a CMOS sensor and is positioned directly below the two-dimensional diffraction element without any other intervening optical elements between the two-dimensional diffraction element and the CMOS sensor.

* * * * *